United States Patent [19]

Carpio

[11] Patent Number: 4,791,296

[45] Date of Patent: Dec. 13, 1988

[54] FAST METHOD OF MEASURING PHOSPHOROUS CONCENTRATION IN PSG AND BPSG FILMS

[75] Inventor: Ronald A. Carpio, Colorado Springs, Colo.

[73] Assignee: Inmos Corporation, Colorado Springs, Colo.

[21] Appl. No.: 81,492

[22] Filed: Aug. 4, 1987

[51] Int. Cl.$^4$ ............................................. G01J 3/433
[52] U.S. Cl. .................................... 250/339; 250/341
[58] Field of Search .................. 250/339, 340, 341; 364/498; 356/317, 318

[56] References Cited

U.S. PATENT DOCUMENTS 4,590,574 5/1986 Edmonds et al. .................. 250/339

OTHER PUBLICATIONS

F. S. Becker, D. Pawlik, H. Schafer and G. Staudigl, "Process and Film Characterization of Low Pressure Tetraethylorthosilicate-Borophosphosilicate Glass," *J. Vac. Sci. Technol. B*, vol. r, No. 3, p. 732, May/Jun. 1986.

K. Nassau, R. A. Levy and D. L. Chadwick, "Modified Phosphosilicate Glasses for VLSI Applications," *J. Electrochem. Soc.*, vol. 132, No. 2, p. 409, Feb. 1985.

A. C. Adams and S. P. Murarka, "Measuring the Phosphorus Concentration in Deposited Phosphosilicate Films," *J. Electrochem. Soc.*, vol. 126, No. 2, p. 334, Feb. 1979.

J. E. Cahill, "Derivative Spectroscopy: Understanding Its Application," *American Laboratory*, p. 79, Nov. 1979.

R. A. Levy, P. K. Gallagher and F. Schrey, "A New LPCVD Technique of Producing Borophosphosilicate Glass Films by Injection of Miscible Liquid Precursors," *J. Electrochem. Soc.*, vol. 134, No. 2, p. 430, Feb. 1987.

A. S. Tenney and M. Ghezzo, "Composition of Phosphosilicate Glass by Infrared Absorption," *J. Electrochem. Soc.*, vol, 120, No. 9, p. 1276, Sep. 1973.

R. M. Levin, "Water Absorption and Densification of Phosphosilicate Glass Films," *J. Electrochem. Soc.*, vol. 129, No. 8, p. 1765, Aug. 1982.

J. E. Tong, K. Schertenleib and R. A. Carpio, "Process and Film Characterization of PECVD Borophosphosilicate Films For VLSI Applications," *Solid State Technology*, p. 161, Jan. 1984.

R. A. Levy, S. M. Vincent and T. E. McGahan, "Evaluation of the Phosphorus Concentration and Its Effect on Viscous Flow and Reflow in Phosphosilicate Glass," *J. Electrochem. Soc.*, vol. 132, No. 6, p. 1472, Jun. 1985.

G. L. Collier and A. C. M. Panting, "The Use of Derivative Spectroscopy for Determining Methyl Groups in Polythene," *Spectrochemica Acta* 14, p. 104, (1959).

G. L. Collier and F. Singleton, "Infra-Red Analysis by the Derivative Method," *J. Appl. Chem.*, 6, p. 495, Nov. 1956.

Nicolet FT-IR Application Note 8311, D. Compton, "Resolution Enhancement Using Fourier Transforms Part I: Fourier Deconvolution".

W. Kern and G. L. Schnable, "Chemically Vapor-Deposited Borophosphosilicate Glasses for Silicon Device Applications," *RCA Review*, vol. 43, p. 423, Sep. 1982.

R. M. Levin and A. C. Adams, "Low Pressure Deposition of Phosphosilicate Glass Films," *J. Electrochem. Soc.*, vol. 129, No. 7, p. 1588, Jul. 1982.

(List continued on next page.)

*Primary Examiner*—Janice A. Howell
*Attorney, Agent, or Firm*—Edward D. Manzo

[57] ABSTRACT

A method of measuring the phosphorus concentration in phosphosilicate and borophosphosilicate films using infrared spectroscopy in conjuction with derivative spectroscopic techniques. This method is easily adapted for use with a Fourier Transform spectrometer. A spectrum of the film is taken with a dual beam infrared spectrometer. The second derivative of the spectrum is plotted to rersolve close peaks. Amplitudes of the P=O band at 1316 cm$^{-1}$ and the O—Si—O band at 818 cm$^{-1}$ are measured. A ratio between these amplitudes is calculated. The ratio is then matched to a calibration curve to determine the phosphorus concentration.

12 Claims, 2 Drawing Sheets

OTHER PUBLICATIONS

F. S. Becker and D. Pawlik, "A New LPCVD Borophosphosilicate Glass Process Based On the Doped Deposition of TEOS-Oxide," Proceedings of the Symposium On Reduced Temperature Processing for FLSI, R. Reif and G. R. Srinivasan, Eds., *Electrochemical Society*, p. 148, (1986).

P. K. Chu and S. L. Grube, "Quantitative Determination of Boron and Phosphorus in Borophosphosilicate Glass by Secondary Ion Mass Spectrometry," *Analytical Chemistry*, vol. 57, No. 6, p. 1071, May 1985.

Dr. K. Krishnam, "Simultaneous Determination of Phosphorus and Boron in Silicon Dioxide Glass Films on Silicon," Bio-Rad Semiconductor Notes, Notes No. 103, May 1983.

K. Krishnan, "Simultaneous Determination of the Boron and Phosphorus Content in Silicate Glasses by FT-IR Spectroscopy," *Semiconductor Processing*, ASTM 850, D. C. Gupta, Ed. ASTM, p. 358, 1984.

Perkin Elmer Application Note No. 8604 10/15/86, "Automated Multi-Sample SIMS Analysis of Phosphosilicate Glass".

FAST METHOD OF MEASURING PHOSPHOROUS CONCENTRATION IN PSG AND BPSG FILMS

FIELD OF THE INVENTION

The present invention relates to a method of measuring phosphorus concentration in phosphosilicate ("PSG") and borophosphosilicate ("BPSG") films. Infrared spectroscopy in conjunction with derivative spectroscopic techniques are used in the preferred embodiment of this invention.

BACKGROUND OF THE INVENTION

Properties of PSG and BPSG films make them useful in a variety of semiconductor technology applications. Since the properties of these films which make PSG and BPSG useful in a given application may depend on the phosphorus concentration, it is important to be able to establish this concentration. It would be optimal to control the phosphorus concentration during processing, but concentration control during processing is not always possible. In quality control applications, therefore, a fast, nondestructive method of measuring the phosphorus concentration in an integrated circuit processing line is often desirable.

There are a variety of analytical techniques which have been utilized for measuring the phosphorus concentration in PSG and BPSG films, as reviewed in A. C. Adams and S. P. Murarka, "Measuring the Phosphorus Concentration in Deposited Phosphosilicate Films," 126 *J. Electrochemical Society* 334 (1974). These include: direct chemical analysis, infrared spectroscopy, electron microprobe, neutron activation analysis, x-ray fluorescence, Auger analysis, etch rate variation and diffusion techniques. Chemical analysis, which is the most direct method, is very tedious and is a destructive method. Chemical analysis has typically been used to establish an absolute calibration for other techniques. Other techniques (electron microprobe, Auger analysis, neutron analysis, and x-ray techniques) require relatively sophisticated equipment. Sophisticated equipment adds to the cost of analysis through higher equipment costs as well as additional operator time and training. For frequent, routine analysis, the simpler and less costly techniques (infrared spectroscopy and x-ray fluorescence) have an advantage, provided of course that the precision and accuracy are acceptable. Infrared spectroscopy has previously been used for measuring the phosphorus concentration in PSG and BPSG films.

Previous infrared spectroscopic methods of phosphorus concentration in PSG films are generally disclosed in R. M. Levin, "Water Absorption and Densification of Phosphosilicate Glass Films," 129 *J. Electrochemical Society* 1765 (August 1985) and A. C. Adams, *VLSI Technology*, S. M. Sze. Editor, Chapter 3 (McGraw-Hill, New York 1983).

These methods for measuring the phosphorus concentration in PSG films typically involve the use of a double beam spectrophotometer. The PSG film is deposited on a silicon wafer and the wafer is placed in the appropriate beam. A silicon wafer matched to the silicon wafer on which the PSG film is deposited or air, may be used as a reference. The chosen reference is used in the reference beam. Next, a spectrum (either transmission or absorption) of the PSG film is taken from somewhere between 250 to 4000 cm$^{-1}$ Next, the amplitude of the P=O band at about 1316 cm$^{-1}$ is measured. This amplitude may then be used with a calibration curve which relates the P=O band amplitude to actual phosphorus concentration. A calibration curve is constructed by determining the P=O band amplitudes for samples used as standards and plotting the amplitudes against the actual phosphorus concentrations of these known standards. The actual phosphorus concentrations of these standards are typically measured by chemical analysis techniques.

Alternately, the amplitudes of the P=O band at about 1316 cm$^{-1}$ and either of the Si—O bands at about 818 cm$^{-1}$ or at about 1080 cm$^{-1}$ are measured. A ratio of these amplitudes is calculated, with the P=O band amplitude as the numerator and the chosen Si—O band amplitude as the denominator. Use of this amplitude ratio obviates the need to know the film thickness. Next, a calibration curve is constructed by determining this amplitude ratio for samples used as standards and plotting these ratios against the corresponding actual phosphorus concentrations of these known standards. The actual phosphorus concentrations of the standards are typically measured by chemical analysis techniques.

An improvement on these basic infrared spectroscopic methods deals with performing a correction to the calibration curve as disclosed in A. S. Tenney and M. Ghezzo, "Composition of Phosphosilicate Glass by IR Absorption," 120 *Journal of the Electrochemical Society* 1276 (1973). Specifically, the amplitude ratio calculated from the band amplitudes is recalculated using the ratio between the P=O and Si—O band areas rather than their band amplitudes. The advantage in employing the band area ratio in lieu of the linear amplitude ratio is that the band area ratio appears to reduce the temperature dependence in the calibration curve. This temperature dependence is more prevalent in BPSG films than in PSG films.

Unfortunately, these previous methods for measuring the phosphorus concentration in PSG films have not been as accurate as required, and the detection limits afforded by these previous methods have not been very low. These previous methods have failed to address and overcome several problems inherent in measuring the phosphorus concentration in PSG films.

Most importantly, these previous methods have failed to address and overcome the inherent problem of overlapping bands in the PSG infrared spectrograph. The problem associated with overlapping bands in PSG films is well known and is generally disclosed in the articles cited above and in K. Nassau, R. A. Levy and D. L. Chadwick, "Modified PSG's for VLSI Application," 130 *J. Electrochemical Societ* 404 (February 1985). Specifically, previous methods have not dealt effectively with the overlap of the P=O band at about 1316 cm$^{-1}$ and the Si—O stretching band whose maximum is at about 1080 cm$^{-1}$. The overlap problem results in not being able to measure accurately the amplitude of the P=O band for use in quantitative analysis. This overlap has been the main impediment to measuring the phosphorus concentration in PSG films.

Measuring the phosphorus concentration in BPSG films with the infrared spectroscopic method is additionally more complex because of the presence of boron. Some previous methods of measuring the phosphorus concentration in BPSG films involve using the uncorrected amplitude measurements at about 1316 cm$^{-1}$ for the phosphorus analysis and at about 1370 cm$^{-1}$ for the boron analysis to derive calibration curves. Other methods have used a procedure similar to that discussed above for analysis of PSG films in which an amplitude ratio is calculated by first measuring the amplitudes of two relevant bands on the spectrum and then dividing one of the amplitudes by the other to normalize for film thickness. See generally, W. Kern and G. L. Schnable, "Chemically Vapor-Deposited BPSG for Silicon Device Application," *RCA Review* 43, p. 423 (September 1982). A calibration curve is then constructed by determining the amplitude ratio for samples used as standards and plotting these ratios against the corresponding the actual phosphorus concentration of the standards as typically measured by chemical analysis techniques.

Like previous methods of measuring the phosphorus concentration in PSG films, previous methods of measuring the phosphorus concentration in BPSG films have not been as accurate as required, and detection limits have not been adequately very low. These previous methods have likewise failed to address and overcome several problems inherent in measuring the phosphorus concentration in BPSG films.

Most importantly, these previous methods have failed to address and overcome the inherent problem of overlap between the P=O and B—O absorption bands at about 1316 and at about 1370 cm$^{-1}$ respectively. The overlap problem in BPSG films is generally disclosed in F. S. Becker and D. Pawlik, "A New LECVD BPSG Process Based on the Doped Deposition of TEOS-Oxide," *Proceedings of the Symposium of Reduced Temperature Processing for VLSI*, R. Reif and G. R. Srinivason, eds., *Electrochemical Society* (1986). This overlap in BPSG films is in addition to the overlap of the P=O band at about 1316 cm$^{-1}$ and the Si—O band at about 1080 cm$^{-1}$ Both sets of overlapping bands have been the main impediment to measuring the phosphorus concentration in BPSG films. Besides this overlap, the phosphorus band is weak in comparison to the boron band, which tends to obscure the phosphorus band.

Furthermore, as revealed in the article by F. S. Becker, D. Pawlik, H. Schafer and G. Staudigl, "Process and Film Characterization of Low Pressure Tetraethylorthosilicate Borophosphosilicate Glass", *J. Vac. Sci. Technol. B* 4(3), 732 May/June 1986, difficulties have been experienced in calibration, i.e., finding a quantitative relationship between spectral features and the boron concentrations in BPSG films. In addition, the strongest absorption of the silicon-oxygen vibration at about 1080 cm$^{-1}$ changes band form and position of the band maximum depending on the dopant concentration. Even the band at 450 cm$^{-1}$, corresponding to another silicon-oxygen vibration, is broadened when boron is one of the glass components. These difficulties have been addressed and overcome by the present invention.

Various methods have been used to resolve close or overlapping bands in infrared spectroscopy. The preferred embodiment of the present invention uses the derivative spectroscopic technique. Derivative spectroscopy has been disclosed in J. E. Cahill, "Derivative Spectroscopy: Understanding Its Application," *American Laboratory*, November, 1979, p. 79. Derivative spectroscopy calculates the first, second or higher order derivative of a spectrum with respect to wavelength or frequency. As each higher order derivative is calculated, each of the spectrograph's bands become more defined individually, and close or overlapping bands become more resolved. The derivative plot is used for further analysis, rather than the spectrum itself. Amplitudes are measured from the derivative plot rather than the original plot spectral curve.

The application of derivative spectroscopy to infrared spectroscopic methods has been limited. Derivative spectroscopy has been used in a procedure different from the present invention, in G. L. Collier and F. Singleton, "Infrared Analyses by the Derivative Method," 6 *J. Appl. Chem.* 495 (November 1956), and G. L. Collier and A. C. M. Panting, "The Use of Derivative Spectroscopy for Determining Methyl Groups in Polythene," 14 *Spectrochemical Acta* 104 (1959).

As discussed above, inherent problems associated with poor resolution of overlapping bands in infrared spectrographs of phosphorus in PSG and BPSG films and the limited sensitivity of these techniques to low concentrations of phosphorus are recognized drawbacks. Furthermore, as typical of all other analytical techniques which yield relative results, infrared spectroscopic techniques require proper standardization, a task hard to achieve with previous infrared spectroscopic techniques.

The present invention addresses and overcomes the problem of overlapping bands and changing band forms in measuring the phosphorus concentration in PSG and BPSG films through the use of derivative spectroscopy. Derivative spectroscopic techniques are used to separate and resolve each of the bands in the spectrograph so that the influence of overlapping bands on each other will be minimized.

The resolution of overlapping bands also lowers the sensitivity of the technique since the influence from other bands is minimized. The present invention then increases the sensitivity of previous methods to detect low concentrations of phosphorus.

Further, the use of the described amplitude ratio obviates the need to monitor film thicknesses, and the use of a calibration curve based on these ratios provides standardization for the present invention. This standardization is advantageous if the process is to be used in quality control applications.

Moreover, for BPSG films, the dependence of the phosphorous concentration on the boron concentration is incorporated into the calibration curve.

In general, the infrared techniques have advantages over other techniques because the instrumentation costs are less on a relative scale, it is nondestructive, fast, accurate, and it can be performed by relatively unskilled operators.

It is accordingly a general object of the invention to provide greater accuracy and a lower detection limit in both PSG and BPSG films by making it possible to deal effectively with the overlap of the P=O band at about 1316 cm$^{-1}$ and the Si—O stretching band whose maximum is at about 1080 cm$^{-1}$.

For BPSG films, the present invention further provides a means to deal effectively with the additional overlap of the P=O band, whose maximum is at about 1316 cm$^{-1}$, and the B—O band whose maximum occurs at about 1370 cm$^{-1}$ This invention finds application by semiconductor manufacturers for process monitoring and development activities. Furthermore, manufacturers of infrared spectrometers might include this procedure as a software package and application and utilize it to sell not only the software but also their instrumentation.

BRIEF DESCRIPTION OF THE DRAWINGS

In describing the present invention, reference is made to the accompanying drawings wherein.

SUMMARY OF THE INVENTION

Figure 1:
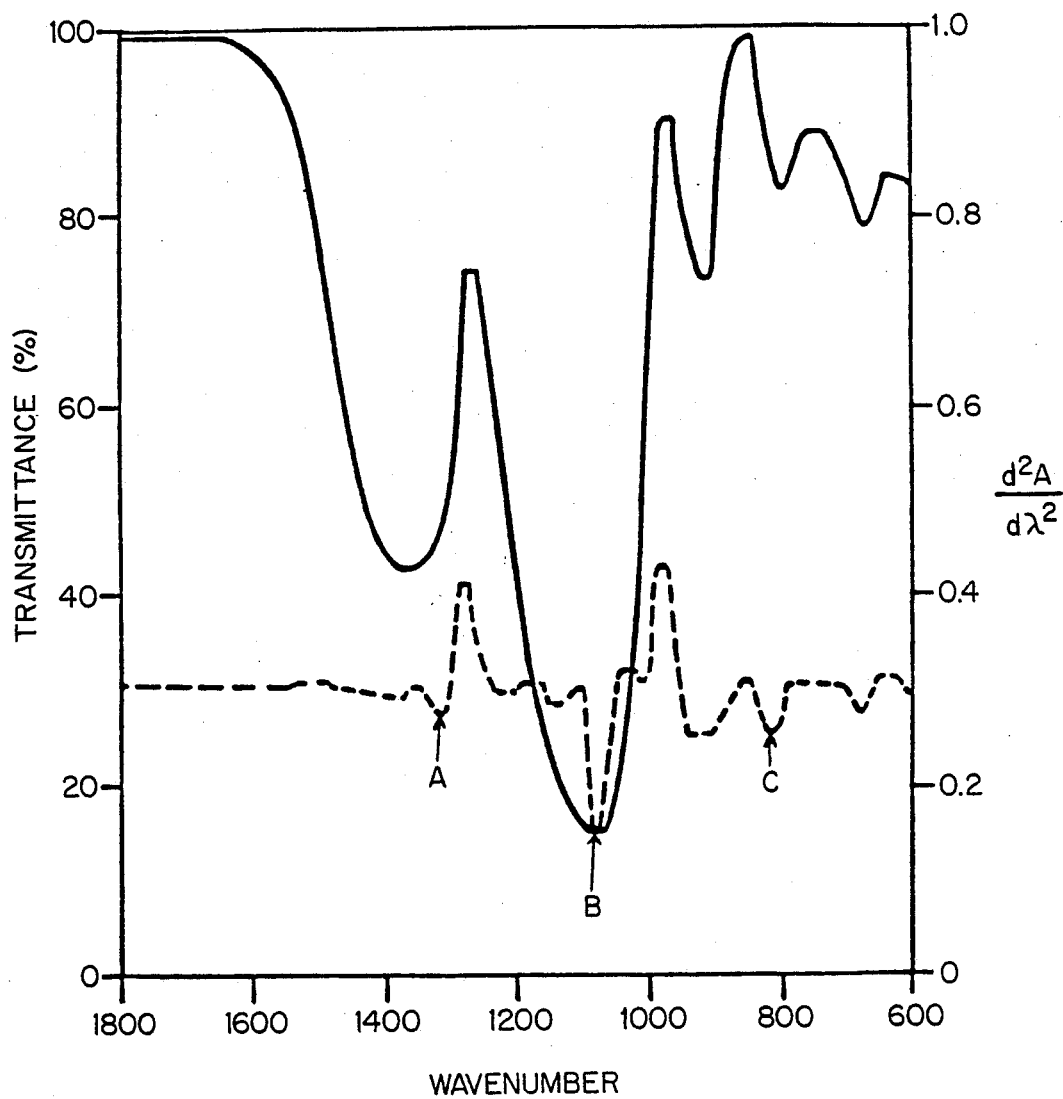
FIG. 1 illustrates the transmission and second derivative spectra of a BPSG film.

The invention involves determining the transmission or absorption spectrum of the PSG or BPSG film over a range, preferably from 1800 $cm^{-1}$ to 600 $cm^{-1}$, with a double beam infrared spectrometer. The film is deposited on a wafer (illustratively formed of silicon) for analysis, and a reference (illustratively an uncoated wafer) is placed in the reference beam. Preferably, the film's spectrum is mathematically "smoothed" by ways well known in the prior art. Thereafter, the second derivative of the spectrum is plotted to resolve close bands within the spectrum. In the preferred embodiment specifically, the second derivative is used to resolve the P=O band at about 1316 $cm^{-1}$ from overlapping bands, regardless of whether the film is PSG or BPSG.

Next, measurements of the second derivative plot are taken at known amplitudes for the P=O band at about 1316 $cm^{-1}$ and the Si—O band at about 818 $cm^{-1}$. A ratio between these amplitudes is calculated and then reference is made to a calibration curve to determine the phosphorus concentration. Calibration curves for PSG and BPSG films will have been established using a destructive technique such as ion chromotography.

DETAILED SUMMARY OF THE PREFERRED EMBODIMENT

While the invention will be described in connection with a preferred embodiment, it will be understood that it is not intended to limit the invention to this embodiment. On the contrary, it is intended to cover all alternatives, modifications, and equivalents as may be included in the spirit and scope of the invention as defined by the appended claims.

The PSG or BPSG film on which the phosphorus concentration is to be determined is established on one side of a polished wafer (illustratively formed of silicon). The silicon wafer is similar to those used in the fabrication of semiconductor devices. It should be noted that 10,000 angstrom films thicknesses have proven to be convenient for these analyses, and that the films must be analyzed immediately after deposition or preserved in an inert gas chamber to prevent moisture absorption which could lead to erroneous results.

A reference material must also be chosen. An uncoated wafer matched as closely to the coated wafer as possible may used as a reference. Alternatively, an air reference may be used. Use of an air reference is especially convenient when the method is carried out on a Fourier Transform Infrared (FTIR) spectrometer. Many semiconductor fabricators now have only FTIR instrumentation, due to the better signal-to-noise ratios that can be attained with this instrumentation. Of course, the background noise level due to the substrate is not eliminated if air is used as a reference, either with a dispersive or FTIR instrument. However, the inventor has found that this background, when incorporated in the calibration curve, has no effect on the accuracy of the method. This may not be true for all types of wafers, since there are many different backside damages currently being employed for gettering purposes. Caution should therefore be exercised when choosing an air reference.

The coated wafer is placed in a dual beam, infrared spectrometer along with the uncoated wafer, if appropriate. A suitable spectrophotometer should be equipped with a data processing system such as described in the article by R. E. Anacreon and S. C. V. Pottacini "Applications of an Infrared Data Processing System" *American Laboratory*, February, 1980, p. 97. Such a system can be purchased for as little as $22K.

Next, a transmission or absorption spectrum of the PSG or BPSG film is measured over the range of 1800 $cm^{-1}$ to 600 $cm^{-1}$. The resulting spectrum is electronically smoothed if necessary. An example of the smoothed spectrum of a BPSG film is shown by the solid-line curve in FIG. 1, where the abscissa represents the wavenumber and the ordinate represents the transmittance (percent). It is noted that the right side of FIG. 1 also indicates the scale of the second derivative of absorbance with respect to wavelength.

A second derivative of either the transmittance or absorbance of the spectrum is electronically calculated. An example of the second derivative of the spectrum of a BPSG film is shown by the dashed-line curve in FIG. 1. This dashed-line curve is the second derivative (absorbance with respect to wavelength) of the solid-line curve also in FIG. 1. Referring to FIG. 1, band A represents the second derivative of the P=O band at about 1316 $cm^{-1}$, band B represents the second derivative of the Si—O stretching band at about 1080 $cm^{-1}$, and band C represents the second derivative of Si—O band at about 818 $cm^{-1}$. One suitable algorithm to derive the second derivative is described in A. Savitzlay and M. J. E. Golay, *Anal. Chem.* 36, 1627 (1964). The purpose of taking the second derivative of the spectrum is to deal effectively with the overlap of the P=O band at about 1316 $cm^{-1}$ (indicated as point P) and the Si—O stretching band (indicated as point S) whose maximum is at about 1080 $cm^{-1}$. Please note that point P itself consists of completely overlapping P=O and B—O vibrational bands. Taking the second derivative of the spectrum resolves the P=O and Si—O bands into two distinct bands, and this enhanced resolution affords greater accuracy and a lower detection limit.

Figure 2:
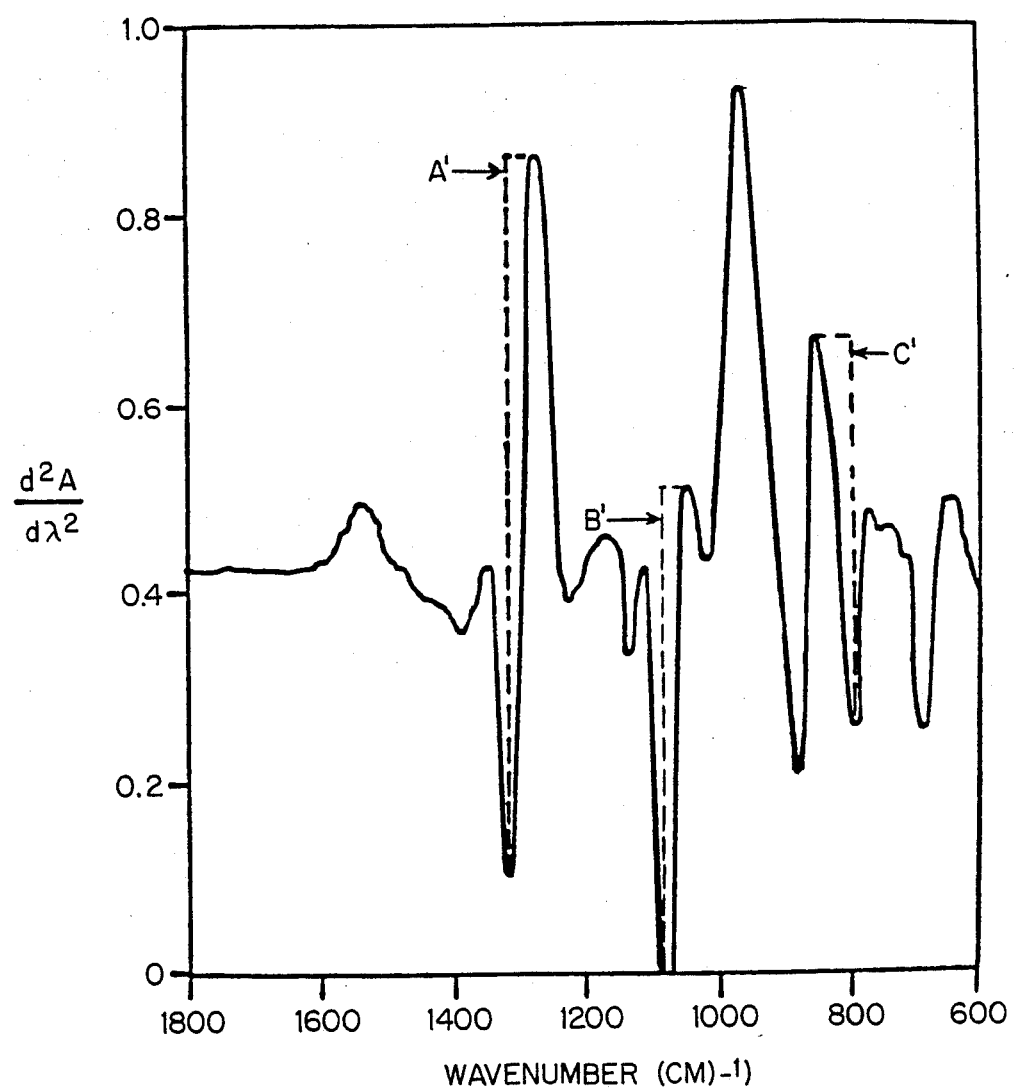
FIG. 2 is referred to in describing the procedure for measuring second derivative band amplitudes of a BPSG film.

The resulting derivative spectrum may be plotted, and the amplitude of the P=O band at about 1316 $cm^{-1}$ is measured. Referring to FIG. 2, which plots the second derivative of the absorbance with respect to wavelength, the amplitude of the P=O band at about 1316 $cm^{-1}$ is represented by the height of the dashed line A' between the base of the band and its peak. The phosphorus concentration can then be established from a calibration curve relating the second derivative amplitude of the P=O band to the corresponding phosphorus concentration. The calibration curve can be constructed by measuring the ratios of sample films used as standards, and then establishing the phosphorus concentration of the standards by a destructive, primary analytical technique. The primary analytical technique of choice is the ion chromotographic technique described in the paper by J. E. Tong, K. Schertenleib, and R. A. Carpio, *Solid State Technology*, 27(1), 161 (1984).

Alternatively, the resulting second derivative spectrum is calculated, and the amplitudes of the P=O band at about 1316 $cm^{-1}$ and either of the the Si—O bands at about 1080 cm$^{-1}$ or at about 818 cm$^{-1}$ may be measured. Referring to FIG. 2, the amplitude of the Si—O band at about 1080 cm$^{-1}$ is represented by the height of the dashed line B' between the base of the band and its peak, and the amplitude of the Si—O band and at about 818 cm$^{-1}$ is represented by the height of the dashed line C' between the base of the band and its peak. A ratio between the second derivative amplitudes of the P=O band and either of the Si—O bands is computed to normalize for film thickness. The second derivative amplitude for the P=O band may be used as the numerator and the second derivative amplitude for either of the Si—O bands may be used as the denominator.

The phosphorus concentration can then be established from a calibration curve incorporating this amplitude ratio and the measured boron concentration. The calibration curve or curves for this ratio method can be fitted to an equation of the type:

Wt % Phosphorus = A×(Wt % Boron)+B×("P=O/Si—O" Ratio)×C where:

(1) A, B, and C are regression coefficients, A being zero in the case of PSG films;

(2) the weight percentage of boron, "Wt % Boron", is determined from the infrared absorption spectrum, as outlined in the *Solid State Technology* paper referenced just above; and (3) the "P=O/Si—O Ratio" is determined from the second derivative spectrum as described.

It should also be noted that this technique establishes the concentration of phosphorus in the +5 oxidation state. In order to find the total phosphorus concentration in cases where phosphorus also exists in the +3 oxidation state, the ratio between the phosphorus in the +3 oxidation state must be established by ion chromotography, or some other analytical technique. Once this ratio is known, it is a simple matter to compute the total phosphorus concentration. In some cases as much as ten percent of the total phosphorus can exist in the +3 oxidation state.

What is claimed is:

1. A method of measuring phosphorus concentration in phosphosilicate film, which comprises:
   (a) depositing the film on a first wafer, and placing the first wafer for analysis in a dual beam infrared spectrometer;
   (b) using a reference in the reference beam of the spectrometer;
   (c) determining, with the spectrometer, a spectrum of the film;
   (d) calculating the second derivative of said spectrum;
   (e) determining from the second derivative calculation a value based on the P=O stretching band; and
   (f) referring to a calibration curve which relates the value to the phosphorus concentration in the phosphosilicate film.

2. A method as described in claim 1 wherein the reference used is a second wafer.

3. A method as described in claim 2 wherein the second wafer is matched to the first wafer.

4. A method as described in claim 1 wherein the reference used is an air reference.

5. A method as described in claim 1 wherein the phosphosilicate film contains boron.

6. A method as described in claim 5 wherein the phosphorous concentration has a boron concentration term.

7. A method as described in claim 1 wherein said value is determined by measuring a first amplitude for the P=O stretching band and a second amplitude for the major O—Si—O stretching band, said value comprising a ratio being calculated between the two amplitudes, said first amplitude being used as the numerator and said second amplitude being used as the denominator, said calibration curve relating the ratio to phosphorus concentration.

8. A method as described in claim 3 wherein the phosphosilicate film contains boron.

9. A method as described in claim 1 wherein the phosphorus concentration in the +3 oxidation state is determined in films containing the +3 oxidation state, and a ratio between the concentrations of the phosphorus in the +5 and the +3 oxidation state is calculated to compute the total phosphorus concentration.

10. A method as described in claim 1 wherein the spectrum is mathematically smoothed before the second derivative is calculated.

11. A method as described in claim 1 wherein the calibration curve is constructed using ion chromotographic techniques to establish actual phosphorus concentration.

12. A method as described in claim 1 wherein the film deposited is approximately 10,000 angstroms thick.

* * * * *